United States Patent [19]
Fletcher et al.

[11] 3,953,792
[45] Apr. 27, 1976

[54] PARTICULATE AND AEROSOL DETECTOR

[76] Inventors: James C. Fletcher, Administrator of the National Aeronautics and Space Administration, with respect to an invention of; Jimmie J. Wortman, Chapel Hill, N.C.; Robert P. Donovan, Durham, N.C.; Arthur D. Brooks, Morrisville, N.C.; Larry K. Monteith, Raleigh, N.C.; William H. Kinard, Williamsburg; Robert L. O'Neil, Yorktown, both of Va.

[22] Filed: Apr. 26, 1974

[21] Appl. No.: 464,722

[52] U.S. Cl. ................. 324/61 R; 209/127 R; 317/246; 324/71 CP
[51] Int. Cl.² ........................................ G01R 27/26
[58] Field of Search ................. 324/61 R, 71 CP; 317/246; 209/81 R, 109, 111.5, 127 R; 235/151.31

[56] References Cited
UNITED STATES PATENTS

| | | | |
|---|---|---|---|
| 2,825,872 | 3/1958 | Stubbs et al. | 324/71 CP |
| 3,225,296 | 12/1965 | Roth | 324/61 R |
| 3,307,407 | 3/1967 | Berg et al. | 317/246 X |
| 3,308,376 | 3/1967 | Katz | 324/61 R |
| 3,456,112 | 7/1969 | Webb | 317/246 X |
| 3,473,096 | 10/1969 | Johnson et al. | 317/246 |
| 3,626,166 | 12/1971 | Berg et al. | 324/71 CP |
| 3,628,139 | 12/1971 | Huber | 324/71 CP |

*Primary Examiner*—Stanley T. Krawczewicz
*Attorney, Agent, or Firm*—William H. King; Howard J. Osborn; John R. Manning

[57] ABSTRACT

The invention is a device for counting aerosols and sorting them according to either size, mass or energy. The component parts of the invention are an accelerator, a capacitor sensor and a readout. The accelerator is a means for accelerating the aerosols toward the face of the capacitor sensor with such force that they partially penetrate the capacitor sensor, momentarily discharging it. The readout device is a means for counting the number of discharges of the capacitor sensor and measuring the amplitudes of these different discharges. The capacitor employed is a metal-oxide-silicon capacitor in which the metal and oxide layers are very thin. The aerosols are accelerated by the accelerator in the direction of the metal layer with such force that they penetrate the metal and damage the oxide layers, thereby allowing the electrical charge on the capacitor to discharge through the damaged region. The impacting aerosols create a discharge path which is self-healing; that is, each incident aerosol initiates a discharge path through the capacitor in such a fashion as to vaporize or blow out the conducting path in the process. Once the discharge action is complete, the low resistance path no longer exists between the two capacitor plates and the capacitor is again able to accept a charge. The active area of the capacitor is reduced in size by the damaged area each time a discharge occurs.

8 Claims, 4 Drawing Figures

PARTICULATE AND AEROSOL DETECTOR

ORIGIN OF THE INVENTION

The invention described herein was made in the performance of work under a NASA contract and is subject to the provisions of Section 305 of the National Aeronautics and Space Act of 1958, Public Law 85–568 (72 Stat. 435; 42 USC 2457).

BACKGROUND OF THE INVENTION

The invention relates to counting of aerosols or particles and sorting them according to either size, mass or energy. Previous devices for performing this function include optical devices such as those employed in light-scattering counters (Royco Counter) the nethelometer, and LIDAR back-scattering; impactors and collectors employing films or filters to collect quantities of particles or aerosols which can be subsequently weighed and analyzed; and quartz crystal mass monitors which provide mass accumulation data in real time.

The disadvantages of the optical devices are that they depend upon light-scattering thereby making it difficult to get a size distribution without knowing the index of refraction of the scattering centers as well as their shape. Common practice is to assume these scattering centers are spherical which simplifies the interpretation but also introduces errors, the magnitude of which are not really known for most particulate samples. The signal-to-noise ratio for the mechanical collectors and impactors has been low and what has been measured is generally an integrated mass loading. Improved processing of the output from the quartz crystal mass monitors may alter this limitation but such variables as particle adherence and loss to the sampling chain continue to constitute errors in practice.

It is the object of this invention to provide a device for counting of aerosols or particles in real time and sorting them according to their size, mass or energy that is simple, inexpensive and does not have the disadvantages of the prior art devices.

SUMMARY OF THE INVENTION

The component parts of the invention are an accelerator, a capacitor sensor, and a readout. The accelerator directs particles to impact the capacitor with such force that they penetrate the capacitor causing discharges that are recorded by the readout.

The basic principle of the sensor operation is that a charged capacitor can have a discharge initiated by the impact of a high velocity particle. With suitable construction methods and under appropriate biasing and impacting conditions, the impacting particle creates a discharge path which is self-healing; that is, the incident particle initiates a discharge path through which the capacitor discharges in such a fashion as to vaporize or blow out the conducting path in the process. Once the discharge action is complete, the low resistance path no longer exists between the two capacitor plates and the capacitor is again able to accept a charge. By monitoring the voltage on a capacitor plate the number of particles directed into the capacitor can be determined.

To operate the detector, a voltage less than the breakdown voltage of the dielectric biases the capacitor in its quiescent state. Upon impact with a high energy particle or aerosol, penetration of the capacitor by the particle causes partial discharge of the capacitor. After discharge and self-healing, the capacitor recharges through a battery and a resistor at a rate determined by the charging circuit RC time constant. These discharges are monitored by the readout.

Two types of accelerating stages have been used. The first utilizes a vacuum pump and nozzle to accelerate the particles of a sample volume. The velocity of the gas flow through the nozzle depends upon the pressure differential across the nozzle as well as the dimensions of the nozzle. Particles or aerosols entrapped in the flowing gas are accelerated with the gas and acquire sufficient energy to initiate the capacitor discharge as discussed previously.

An alternate accelerating stage that can be used incorporates a high pressure gas stream and a nozzle to direct particles onto the capacitor plates of the sensor.

The technology used to build the capacitor of the detector is also a key element of the invention. The capacitors employed are of the metal-oxide-silicon (MOS) variety which have been widely research and marketed in the semiconductor industry over the past few years. This disclosure capitalizes on this broad and highly developed technology base by using similar methods to prepare MOS capacitors with thin dielectric and thin top metal electrodes. The thickness of the metal electrode and the dielectric determine to a large degree the minimum energy of particle impact that can initiate a discharge. Above this threshold, the magnitude of the discharge does not depend upon the energy of impact.

The number of pulses generated at the output are recorded by a simple binary scaler. Particles are sized according to mass and velocity by means of three parameters: (1) thickness of the MOS metal and dielectric, (2) acceleration imparted to the particles by the accelerator, and (3) the spacing between the MOS sensor and the nozzle opening. For a given vacuum level a given MOS thickness and given spacing the device will detect all particles that reach a mass velocity threshold just enough to penetrate and discharge the capacitor. Sizing can be accomplished by either changing the pressure or using multiple MOS capacitors, each with a different dielectric thickness.

BRIEF DESCRIPTION OF THE DRAWINGS

Figures 1, 2, 3, 4:
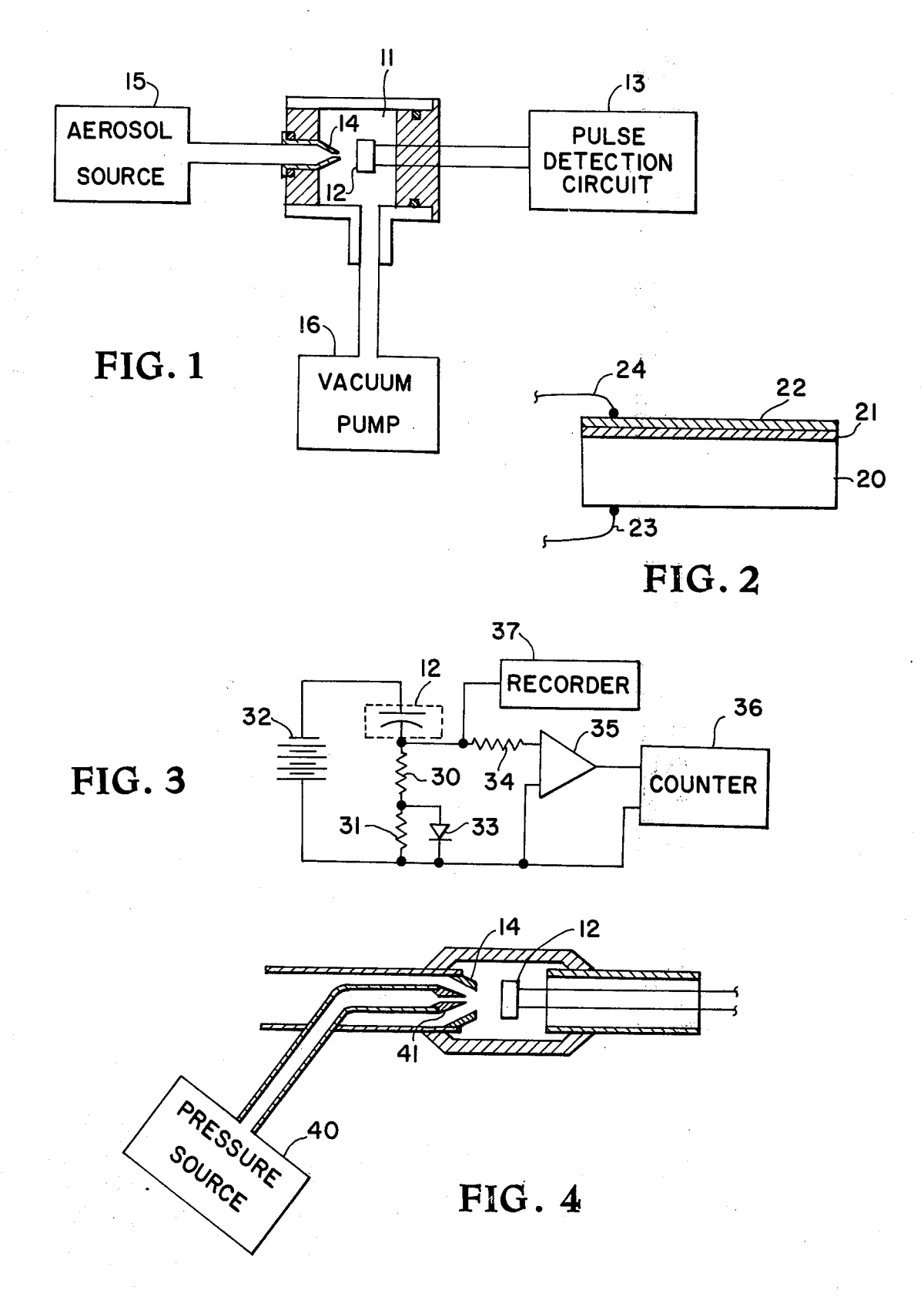

FIG. 1 is a schematic drawing of an embodiment of the invention;

FIG. 2 is a cross section through the capacitor used as the sensing element in this invention;

FIG. 3 is a schematic drawing of the pulse detection circuit used in this invention; and FIG. 4 is a schematic drawing of an alternate embodiment of an accelerometer used in this invention.

DETAILED DESCRIPTION OF THE INVENTION

Turning now to the embodiment of the invention selected for illustration in the drawings, the number 11 designates an enclosure. Mounted inside enclosure 11 by any suitable means, not shown, is a particle detecting capacitor 12. A pulse detecting circuit 13 is electrically connected to capacitor 12 through a wall of enclosure 11. A nozzle 14 extends through a wall of enclosure 11 such that any gas that passes through nozzle 14 will strike capacitor 12. An aerosol source 15 is connected to nozzle 14 to supply the source of aerosol particles to be counted and classified. A vacuum pump 16 is connected to enclosure 11 so as to maintain a vacuum within the enclosure. Consequently, the gas from source 15 containing the aerosol particles will flow through nozzle 14 and strike capacitor 12. The velocity at which the gas from source 15 passes through nozzle 14 depends both on the pressure difference between enclosure 11 which is evacuated and the aerosol source 15 (which is at atmospheric pressure) and the dimensions of the nozzle 14. It has been found that with a throat diameter of 0.059 inch and with a vacuum created by the vacuum pump of approximately 16 inches of mercury the gas will flow through nozzle 14 at approximately 1000 feet per second. However, different sizes of nozzle 14 and magnitudes of the vacuum created by a vacuum pump 16 can be used without departing from the invention.

The capacitor 12 as shown in FIG. 2 includes a silicon wafer 20, a silicon oxide dielectric layer 21 and a metal layer 22. Electrical leads 23 and 24 are connected to wafer 20 and layer 22, respectively. With the metal layer 22 less than 1000 angstroms thick and the silicon oxide layer 21 less than 2000 angstroms thick, 20 micron sized particles from aerosol source 15 traveling at 1000 feet per second through nozzle 14 will always penetrate both layers 21 and 22. Basically this capacitor can be fabricated by evaporating an aluminum or other metal layer 22 on a layer 21 of dielectric silicon oxide which is grown on silicon material 20. Standard I-C processes can be used in the fabrication of these capacitor units. Following is a description of a fabrication process that can be used.

Layer 20 can be a p-type 1¼ inch diameter wafer polished on one side. The wafer is cleaned by a standard silicon cleaning cycle which includes the use of solvents and acids. The wafer is then loaded into the quartz tube of an oxidation furnace for the oxidation cycle. The furnace is at 1100°C. with 2000 cc per minute of dry $O_2$ flowing through it. The oxidation time can be varied to produce different thicknesses of layer 21.

The next step is to evaporate a metal plate 22 on the silicon oxide layer 21. The silcon wafer 20 with the silicon oxide layer 21 is baked in a vacuum oven at 200°C. under a vacuum of approximately 25 inches of mercury for 30 minutes in order to drive off any moisture that may have been absorbed by the silicon oxide layer. The wafer in then placed in the evaporator on an evaporation mask containing a 50 × 50 array of 15-mil diameter holes on 20-mil centers. A standard aluminum evaporation cycle to obtain a 500 angstrom thickness is then carried out. The silicon wafer is then removed from the evaporator and waxes to a glass slide with Apeiezon wax. The side with the aluminum dots are turned down and protected by the wax while the silicon oxide is etched from the back of the wafer with hydrochloric acid. After the etch step, the Apeiezon wax is cleaned from the wafer with boiling trichloroethylene. The wafer is placed back in the evaporator and then 1000 angstroms of aluminum is evaporated on the back of the wafer for electrical contact to the silicon. The wafer is then removed from the evaporator and annealed in the vacuum oven at 200°C. under 24 inches of mercury for 20 minutes to improve the adherence of the aluminum and thus enhance the wire-bonding step.

The next step in the fabrication sequence is to scribe the wafer with a diamond scribing machine to form 100-mil squares containing approximately a 5×5 array of the 15 mil diameter MOS capacitor.

The 100-mil square silicon chips are mounted to 12 pin gold coated TO-5 headers by a eutectic scrub technique. This operation is carried out on a TO-5 header holder which is heated to 450°C. The 100-mil square silicon chip is placed on the hot TO-5 header and then scrubbed on the header surface in a random motion until a eutectic bond is formed between the silicon and the gold of the TO-5 header. This operation not only makes a very strong mechanical bond but also forms a good electrical contact as well.

The last step of the fabrication cycle is bonding of 1 mil diameter gold wire leads from the MOS capacitor to the posts of the TO-5 header. This is accomplished by the use of a nail head bonder at a temperature of 320°C. Eleven of the MOS capacitors are connected to 11 posts on the TO-5 header, and the 12th post is connected to the TO-5 header base which serves as a common contact for the 11 capacitors. The 11 units occupy approximately 20 percent of the area of the silicon chip. This fact should be recognized in the analysis of counting of the micro-particles by MOS units.

The pulse detection circuit 13 (FIG. 1) is shown in detail in FIG. 3 and includes the capacitor 12 connected in series with resistors 30 and 31 and across a voltage source 32. The potential of the voltage source 32 is less than the breakdown voltage of the dielectric in capacitor 12. Upon impact with a high energy particle that penetrates both the metal and oxide layers of capacitor 12, the two plates of the capacitor are effectively shorted and the capacitor begins to discharge. This discharge of current through the capacitor heals the capacitor thereby causing the capacitor to again charge to the level of the voltage source 32. A diode 33 is connected across resistor 31 for the purpose of shorting resistor 31 and increasing the recharging current through capacitor 12 when the short produced by the particles is large. Consequently each time a particle penetrates the capacitor 12 a voltage change is produced at the junction of capacitor 12 and resistor 30 which is applied through a resistor 34 to a high speed differential comparator integrator circuit 35 the output of which produces a pulse that is counted by a high speed counter 36. The count on counter 36 represents the density of the particles in the aerosol source 15. The voltage at the junction of resistor 30 and capacitor 12 is also recorded by a recorder 27 which gives an indication of the sizes of the particles penetrating the capacitor.

FIG. 4 shows a second embodiment of the accelerator that can be used in this invention. In this embodiment of the invention, the particles are supplied to the nozzle 14 by an aerosol source and the capacitor is connected to the pulse detection circuit 13 as disclosed in FIG. 2. However, instead of the vacuum pump 16 in FIG. 1, a pressure source 40 that supplies a nozzle 41 is used to force the gas from the aerosol source 15 through the nozzle 14. A suitable pressure for pressure source 40 is 10 to 50 pounds per square inch.

Other methods of particle acceleration are possible, such as electrostatic acceleration, gravity acceleration (dropping or parachuting the detector through the volume of interest) or attachment to high speed vehicles. Any method which causes the detector to be moving with respect to the particles is capable of inducing the impacts. For example, particulate matter in rocket exhaust or wind tunnels could be detected by simply placing the device in the flow stream. In the case of high temperature environment measurements such as in an exhaust stream a protective plate with a small hole could be placed in front of the sensor. This arrangement would be analogous to a pin hole camera.

Similarly, the MOS capacitor can be made with different dielectrics and different materials and most likely different semiconductors. Only silicon has been demonstrated, but similar structures can be made with metal dielectric semiconductor capacitors.

The advantages of this invention are that the high signal-to-noise ratio of the device is a major advantage over the previous detectors. This detector can count single particles with very high efficiency and can distinguish one particle from another with respect to both time of impact and energy of impact.

What is claimed is:

1. A device for measuring aerosol particles suspended in a gas comprising:
   a capacitor including a first conducting layer, a dielectric layer less than 2,000 angstroms thick grown on said first conducting layer, and a second conducting layer less than 1,000 angstroms thick evaporated onto said dielectric layer;
   a circuit means connected to said two conducting layers of said capacitor for charging said capacitor;
   an accelerator means for accelerating said gas to a velocity such that each of said aerosol particles will penetrate both said second conducting and said dielectric layers of said capacitor, said accelerator means being positioned such that said accelerated gas is directed onto said second conducting layer whereby each aerosol particle will short said two conducting layers of said capacitor thereby causing the capacitor to discharge until the conducting path is vaporized causing the capacitor to recharge to its initial level; and
   detection means connected to said circuit means for counting the number of discharges of said capacitor whereby the density of said aerosol particles in said gas is determined.

2. A device according to claim 1 wherein said second conducting layer is metal, said dielectric layer is silicon oxide and said first conducting layer of the capacitor is silcon.

3. A device according to claim 1 including means for recording the voltage across said capacitor thereby providing data from which the number of the aerosol particles can be determined.

4. A device according to claim 1 wherein said accelerator means comprises a nozzle located relative to said capacitor such that the gas that passes through said nozzle will strike said second conducting layer of said capacitor and means for forcing said gas through said nozzle.

5. A device according to claim 4 wherein said means for forcing said gas through said nozzle is a vacuum source located on the capacitor side of said nozzle.

6. A device according to claim 4 wherein said means for forcing said gas through said nozzle is a pressure source located on the side of the nozzle opposite the capacitor.

7. A device according to claim 4 wherein the size of said nozzle and the magnitude of said means for said forcing said gas through said nozzle are such that the gas is forced through said nozzle at approximately 1000 ft. per sec.

8. A device according to claim 4 wherein said nozzle is approximately 0.06 inch in diameter.

* * * * *

PO-1050
(5/69)

UNITED STATES PATENT OFFICE
CERTIFICATE OF CORRECTION

Patent No. 3,953,792          Dated April 27, 1976

Inventor(s) James C. Fletcher

It is certified that error appears in the above-identified patent and that said Letters Patent are hereby corrected as shown below:

The name "Robert L. O'Neil" in [76] on the cover sheet should read --Robert L. O'Neal--.

Signed and Sealed this

Thirteenth Day of July 1976

[SEAL]

Attest:

RUTH C. MASON
*Attesting Officer*

C. MARSHALL DANN
*Commissioner of Patents and Trademarks*